United States Patent [19]
Adams

[11] Patent Number: 5,470,315
[45] Date of Patent: Nov. 28, 1995

[54] OVER-THE-WIRE TYPE BALLOON CATHETER WITH PROXIMAL HYPOTUBE

[75] Inventor: Daniel O. Adams, Orono, Minn.

[73] Assignee: SCIMED Life Systems, Inc., Maple Grove, Minn.

[21] Appl. No.: 309,240

[22] Filed: Sep. 20, 1994

[51] Int. Cl.⁶ ................................................. A61M 29/00
[52] U.S. Cl. ............................................. 604/96; 606/194
[58] Field of Search ........................... 604/96, 280–284, 604/264, 97–103; 606/194, 195, 192

[56] References Cited

U.S. PATENT DOCUMENTS

| | | | |
|---|---|---|---|
| 4,943,278 | 7/1990 | Euteneuer et al. | |
| 4,968,300 | 11/1990 | Moutafis et al. | 604/96 |
| 5,047,045 | 9/1991 | Arney et al. | |
| 5,069,673 | 12/1991 | Shwab | 604/280 |
| 5,135,535 | 8/1992 | Kramer | 606/194 |
| 5,156,594 | 10/1992 | Keith | |
| 5,159,937 | 11/1992 | Tremulis | |
| 5,201,723 | 4/1993 | Quinn | 604/264 |
| 5,281,203 | 1/1994 | Ressemann | 604/164 |
| 5,290,247 | 3/1994 | Crittenden | 604/171 |
| 5,334,147 | 8/1994 | Johnson | 604/96 |
| 5,370,615 | 12/1994 | Johnson | |
| 5,383,890 | 1/1995 | Miraki et al. | 606/194 |
| 5,403,339 | 4/1995 | Nobuyoshi et al. | 604/96 X |
| 5,409,470 | 4/1995 | McIntyre et al. | 604/96 X |

FOREIGN PATENT DOCUMENTS

WO93/15786 8/1993 WIPO.

*Primary Examiner*—John D. Yasko
*Attorney, Agent, or Firm*—Robert E. Atkinson

[57] ABSTRACT

A balloon dilatation catheter system is disclosed which includes a proximal metallic tube and a polymer guide wire tube extending alongside the metallic tube. A distal polymer tube is connected to the distal end of the metallic tube and has a dilatation balloon connected to its distal end. The polymer guide wire tube, which is adapted to slidably receive a guide wire, also extends alongside the distal polymer tube and extends through the interior of the inflatable balloon. The balloon catheter may include a core wire extending from a distal end of the metallic tube and parallel with the distal polymer tube. The distal end of the core wire may be directly or indirectly connected to the balloon to transfer force from the distal end of the metallic tube to the balloon. The polymer guide wire tube may be connected to the metallic tube and/or the distal polymer tube by a suitable adhesive, a series of connection rings, or a connection sleeve. Alternatively, the distal polymer tube and the polymer guide wire tube may be integrally formed as a dual lumen extrusion.

15 Claims, 9 Drawing Sheets

SECTION B-B

SECTION D-D

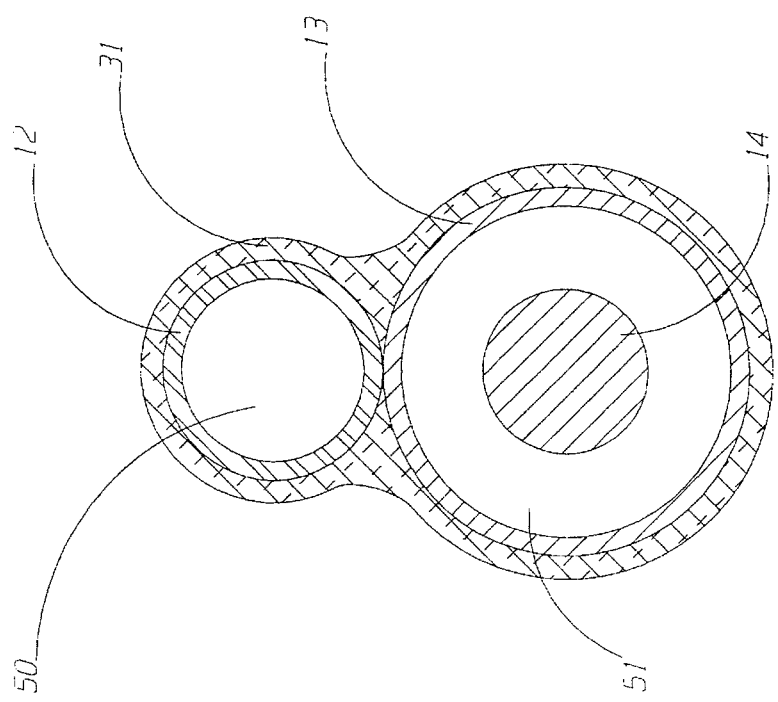

OVER-THE-WIRE TYPE BALLOON CATHETER WITH PROXIMAL HYPOTUBE

CROSS REFERENCE TO RELATED APPLICATIONS

The subject matter of this application is related to the disclosure in commonly assigned and co-pending U.S. patent application entitled INTRAVASCULAR CATHETER WITH DISTAL GUIDE WIRE LUMEN AND TRANSITION MEMBER filed Feb. 16, 1994 Ser. No. 08/197,169 which is hereby fully incorporated by reference.

FIELD OF THE INVENTION

The present invention generally relates to intravascular catheters. More specifically, the present invention relates to over-the-wire type balloon catheters. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well known in the art and may typically involve the use of a balloon catheter and a guide wire, possibly in combination with other intravascular devices. The balloon catheter is advanced over the guide wire such that the distal end of the balloon catheter is positioned adjacent a restriction in a diseased vessel. The balloon is inflated and the restriction in the vessel is thus opened.

Balloon catheters are commonly categorized into three main types according to their guide wire compatibility; over-the-wire (OTW), fixed-wire (FW), and single-operator-exchange (SOE). OTW, FW, and SOE as used hereinafter refers to the conventional design of such catheters. Examples of OTW, FW and SOE catheters may be found in U.S. Pat. Nos. 5,047,045 to Arney et al., 4,943,278 to Euteneuer et al., and 5,156,594 to Keith et al., respectively. The entire disclosure of the above listed patents is hereby incorporated by reference.

OTW catheters are used in combination with a guide wire which is removably insertable therein. The guide wire extends through a full length guide wire lumen inside the OTW catheter. As such, distal pressure measurements, distal fluid injections, and guide wire exchanges may be facilitated through the guide wire lumen. OTW catheter exchanges may be facilitated by the use of an extension wire or a guide wire captivation device.

SOE catheters are also used in combination with a guide wire, but the guide wire extends through a distal guide wire lumen which is inside only a distal portion of the catheter and the remainder of the guide wire remains exposed outside the catheter. As such, a SOE catheter may be readily exchanged over a conventional length guide wire. However, SOE catheters do not readily provide a conventional means to exchange a guide wire without the use of ancillary equipment. Furthermore, SOE catheters do not provide a conventional means for distal pressure measurement and/or distal fluid injection.

By contrast, FW catheters are typically used without a guide wire and as such have a relatively small profile. FW catheters incorporate a built-in core wire which serves some of the same functions as a guide wire. The core wire, however, is not removable and thus the FW catheter is not exchangeable over the core wire. In addition, FW catheters do not provide a conventional means for distal pressure measurement and distal fluid injection.

Although FW catheters generally provide an advantage in profile and although SOE catheters generally provide an advantage in rapid catheter exchange, OTW catheters are considered the more versatile of the group and as such are favored for the majority of clinical applications.

In terms of catheter shaft construction, the proximal shaft portion of an OTW catheter must be designed to contain the guide wire and also provide a path for inflation fluid to inflate the distally located balloon. Thus, the proximal shaft portion of an OTW balloon catheter includes a guide wire lumen and an inflation lumen. By contrast, both SOE catheters and FW catheters only include an inflation lumen in the proximal portion of the shaft. SOE catheters do not require a guide wire lumen in the proximal portion of the shaft because the guide wire is external to the proximal catheter shaft. FW catheters do not require a guide wire lumen in the proximal portion of the shaft because FW catheters are not constructed to be used with removable guide wires. Since the proximal shaft portion of an OTW catheter must accommodate a guide wire lumen and since FW and SOE catheters do not need to accommodate a guide wire lumen, the profile (outside diameter) of the proximal shaft of an OTW catheter is inherently larger than the profile of either a FW or SOE catheter.

In addition to the inherent profile requirements discussed above, the optimal design of a proximal shaft section of an OTW balloon catheter must account for other performance criteria. For example, it is desirable to have a proximal shaft section which is the smallest possible profile, highly pushable (i.e. longitudinally stiff) yet easily coiled for temporary storage and resistant to damage resulting from in-vitro handling (i.e., latitudinally flexible). High performance FW and SOE catheters typically utilize a metallic proximal shaft section (commonly referred to as a hypotube) with an outside diameter on the order of 0.032 inches and a wall thickness on the order of 0.003 inches. Practicing physicians have found the profile, pushability, ease of handling and other performance aspects of these hypotube-type FW and SOE catheters superior by comparison to non-hypotube-type FW and SOE catheters. Similarly, OTW catheters which utilize a hypotube for a proximal shaft section provide enhanced pushability with low profile. However, since the profile of an OTW catheter is inherently larger than a FW or SOE catheter, the latitudinal stiffness of an OTW catheter utilizing a hypotube proximal shaft is undesirably high. As such, the hypotube shaft on an OTW catheter tends to be more difficult to manage in-vitro and more prone to damage during handling.

In view of the advantages of a metallic proximal shaft section and in view of the advantages of an OTW catheter design discussed earlier, it is desirable to have an OTW catheter with a metallic proximal shaft section which is easy to manipulate in-vivo, easy to manage and resistant to damage from in-vitro handling.

SUMMARY OF THE INVENTION

The present invention overcomes the competing disadvantages of the prior art in a novel and non-obvious manner, to provide a catheter that, for example, is easy to manipulate in-vivo, easy to manage and resistant to damage in-vitro. One embodiment of the present invention is a balloon dilation catheter system, including a proximal metallic tube, a polymer guide wire tube extending exteriorly and parallel with the metallic tube, the polymer guide wire tube having a guide wire lumen extending therethrough, a distal polymer tube extending exteriorly and parallel with the polymer guide wire tube, the proximal end of the distal polymer tube connected to the distal end of the proximal metallic tube, a balloon having a proximal end sealably connected to the distal end of the distal polymer tube, the distal end of the balloon sealably connected to the distal end of the polymer guide wire tube, and a removable guide wire slidably disposed in and extending through the guide wire lumen of the polymer guide wire tube.

In another embodiment of the present invention, the proximal end of the balloon is sealably connected to both the distal end of the distal polymer tube and a distal portion of the polymer guide wire tube.

In another embodiment of the present invention, the catheter further includes a core wire having a proximal end rigidly secured to the distal end of the metallic tube. The core wire may extend through the distal polymer tube. In addition, the distal end of the core wire may be connected to one or more of the polymer guide wire tube, the distal polymer tube, and the balloon.

A further embodiment of the present invention includes a proximal sleeve disposed about and connecting the polymer guide wire tube and the metallic tube.

In another embodiment of the present invention, the polymer guide wire tube is a dual-lumen extrusion which includes a connection lumen with the metallic tube extending through the connection lumen.

In a further embodiment of the present invention, the distal polymer tube and the polymer guide wire tube are integrally formed as a dual-lumen extrusion.

While the disclosure focuses on OTW balloon catheters, one skilled in the art will recognize that invention may be incorporated into other devices and uses not discussed herein. Furthermore, in addition to the advantages described, other advantages of the present invention may be appreciated without departing from the spirit of the invention.

BRIEF DESCRIPTION OF THE DRAWINGS

FIG. 9 is a latitudinally sectioned view taken at E—E in FIG. 3.

DETAILED DESCRIPTION OF THE INVENTION

The following detailed description should be read with reference to the drawings in which like elements in different figures are numbered identically.

Figure 1:
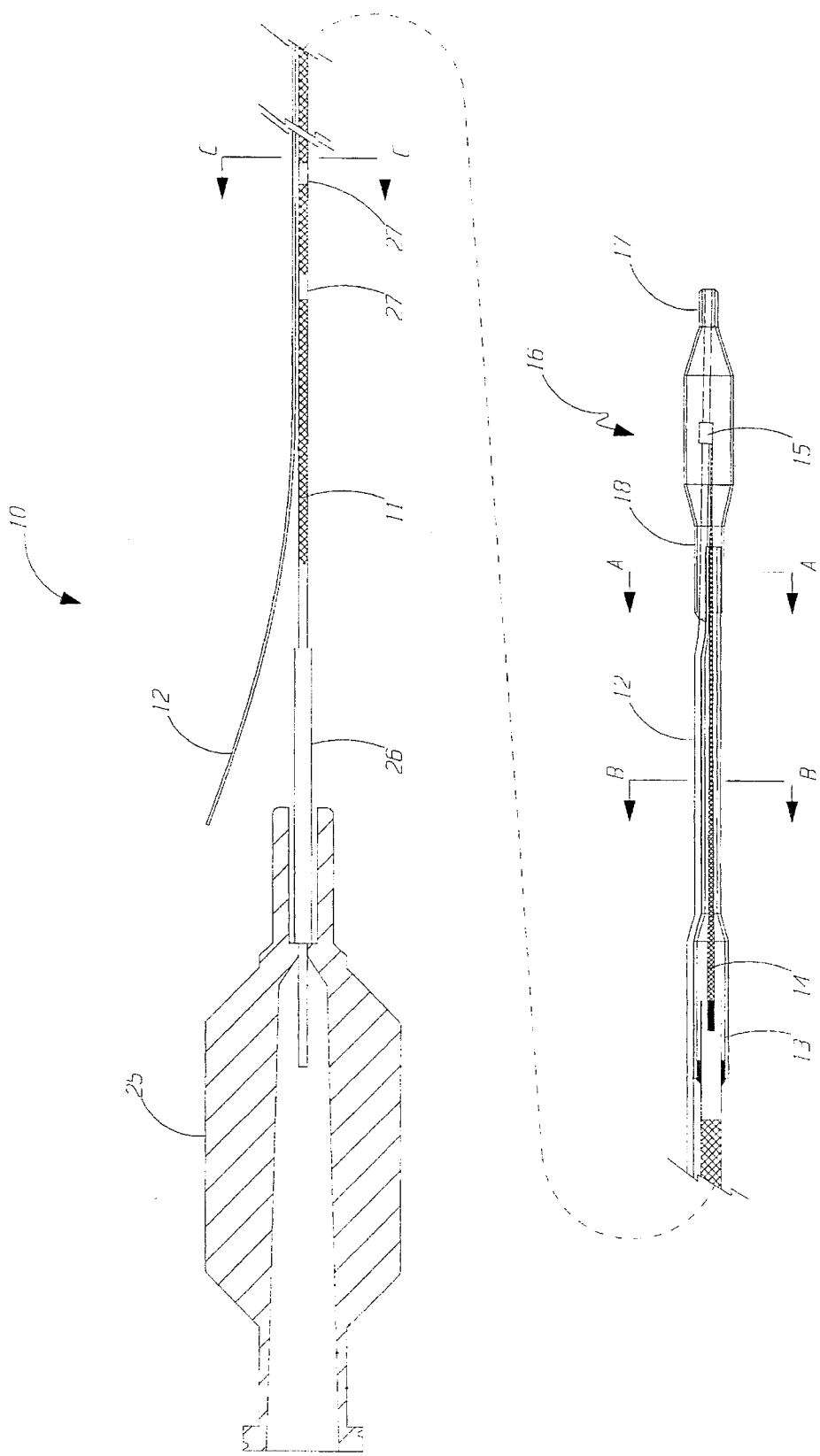
FIG. 1 is a partially longitudinally sectioned view of a first embodiment of the present invention.
Figure 5:
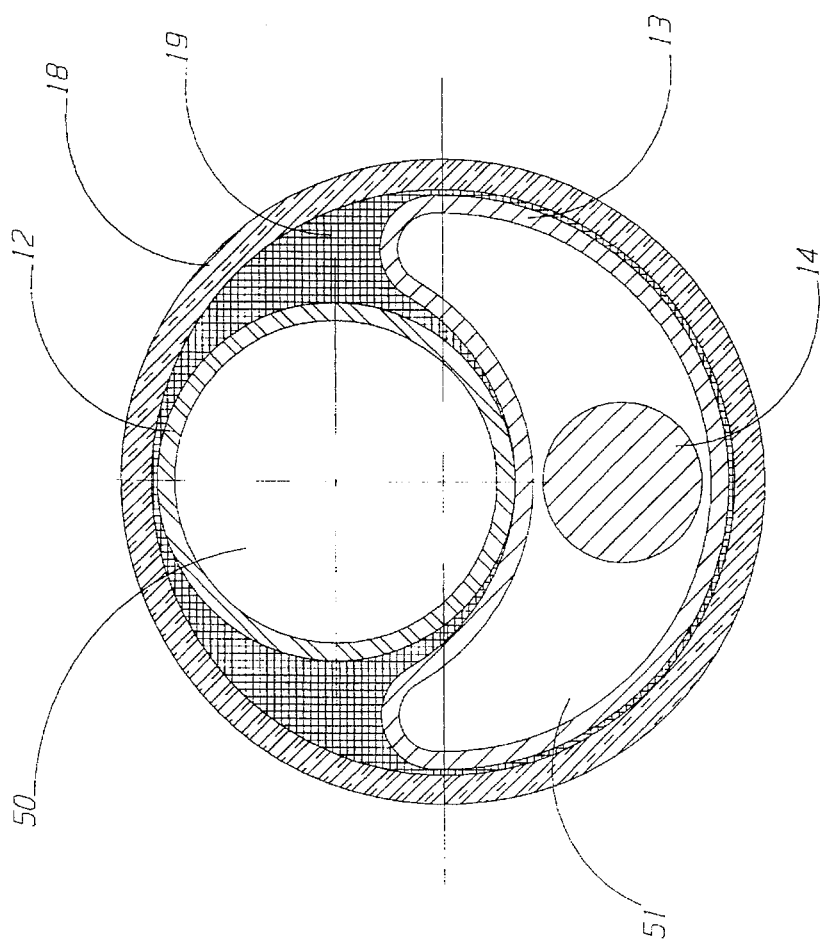
FIG. 5 is a latitudinally sectioned view taken at A—A in FIGS. 1, 2 and 3.
Figure 6:
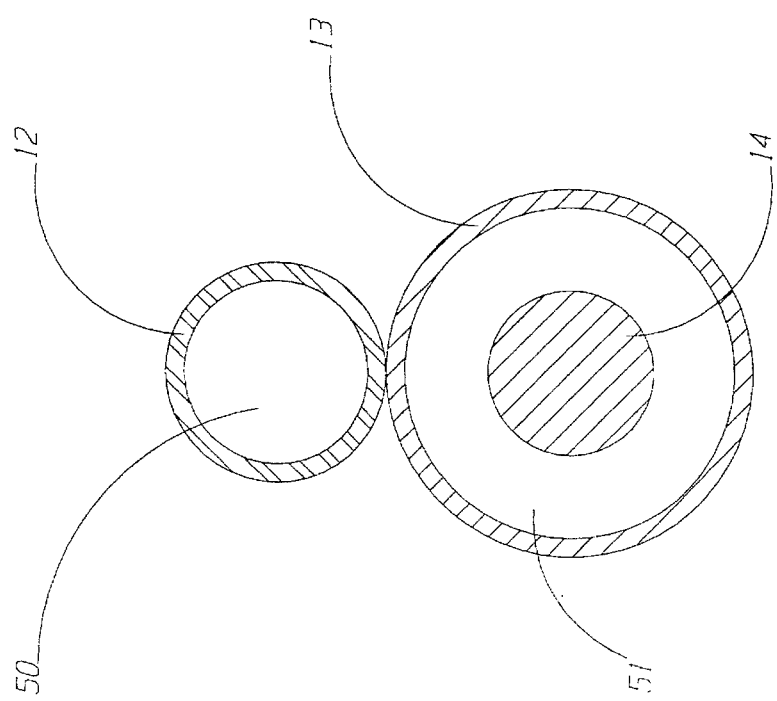
FIG. 6 is a latitudinally sectioned view taken at B—B in FIGS. 1 and 2.
Figure 7:
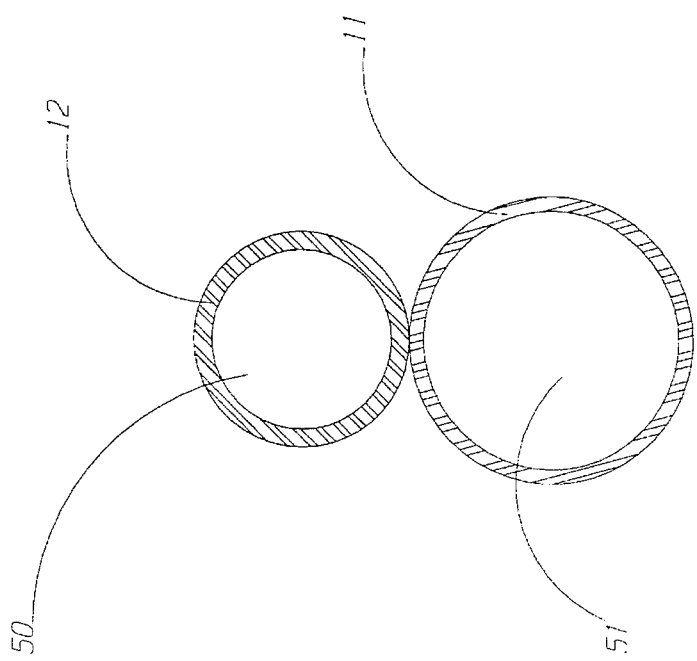
FIG. 7 is a latitudinally sectioned view taken at C—C in FIGS. 1, 2 and 4.

Referring to FIG. 1, catheter 10 includes a metallic tube 11 (also referred to as a hypotube) with a manifold 25 and strain relief 26 connected to its proximal end. The manifold 25 provides a means to connect the catheter 10 to an inflation device (not shown). Strain relief 26 reduces the propensity for the proximal end of the metallic tube 11 to kink during handling. The metallic tube 11 is preferably PTFE-coated and includes proximal shaft marks 27 to indicate the position of the distal end of the catheter 10 relative to the proximal end of the guide catheter (not shown). Core wire 14 is connected to the distal end of the metallic tube 11. The distal polymer tube 13 is also connected to the distal end of the metallic tube 11 and extends partially over the core wire 14. The distal end of the distal polymer tube 13 is connected to the proximal balloon waist 18 of the balloon 16. Catheter 10 further includes a polymer guide wire tube 12 which is connected at its distal end to the distal balloon waist 17. The polymer guide wire tube 12 extends proximally through the balloon and extends exteriorly along the distal polymer tube 13 and the metallic tube 11. The distal polymer tube 13 is crimped into a crescent shape at the proximal balloon waist 18 to facilitate passage of the guide wire tube 12 therethrough (as best shown in FIG. 5). A radiopaque marker band 15 is disposed about the polymer guide wire tube 12 at a position centered within the balloon 16. The radiopaque marker band 15 facilitates fluoroscopic positioning of the balloon catheter at the desired internal vascular site. The core wire 14 is connected at its distal end between the radiopaque marker band 15 and the polymer and guide wire tube 12 to facilitate longitudinal transmission of force between the distal end of the metallic tube 11 and the distal end of the catheter 10 and in particular, the balloon 16. Catheter 10 further includes an inflation lumen 51 as best seen in FIGS. 5, 6 and 7. The inflation lumen 51 allows for the passage of inflation fluid from the manifold 25 to the balloon 16 by way of metallic tube 11 and distal polymer tube 13. The polymer guide wire tube 12 includes a guide wire lumen 50 as best seen in FIGS. 5, 6 and 7. The guide wire lumen 50 allows for passage of a guide wire (not shown) which facilitates navigation of the catheter 10 into the vascular system.

Continuing to refer to FIG. 1, the catheter 10 has a relatively short section where the guide wire tube 12 extends coaxially with the balloon 16 and in particular the proximal balloon waist 18. It should be noted however that the length of the coaxial section may vary depending on the desired performance characteristics. For example, the coaxial section may be substantially as shown in U.S. Pat. No. 5,156, 594 to Keith et al. The catheter shown in Keith '594 does not include a parallel lumen proximal section like the present invention, but the distal section of the Keith '594 catheter may be used in combination with the proximal shaft section of the present invention in order to provide a longer coaxial section distally. In addition, the length of the coaxial section may be between the length which is disclosed in Keith '594 and the length disclosed in the present application. Incorporating a distal coaxial section of a different length does not compromise the benefits provided by the present invention.

Metallic tube 11 is preferably made of 304 V Stainless Steel and includes a PTFE coating on its exterior surface. The proximal portion of metallic tube 11 where manifold 25 and strain relief 26 are connected is preferably left uncoated to facilitate proper adhesive connection. Similarly, the distal end of metallic tube 11 is left uncoated to facilitate proper adhesive connection to distal polymer tube 13 and proper weld or solder connection to core wire 14. In addition, proximal shaft marks 27 are formed by masking portions of the metallic tube 11 prior to PTFE coating. Metallic tube 11 preferably has an outside diameter of 0.024 inches, an inside diameter of 0.017 inches and an overall length of 110 cm. Proximal shaft marks 27 are placed at 90 cm and 100 cm from the distal end of the catheter 10. Proximal shaft marks 27 preferably have a length of between 0.5 cm and 1.0 cm. Metallic tube 11 may be stress-relieved by exposing the metallic tube 11 to a temperature of about 725 degrees Fahrenheit for a period of about an hour. The above exemplary combination of materials, dimensions and processing is designed to provide a metallic tube 11 which can sustain aggressive handling without damage. For example, it is preferable that the metallic tube 11 can be bent in an 8-inch diameter loop without sustaining permanent deformation. Those skilled in the art will recognize that other suitable materials, dimensions and manufacturing processes may be employed to meet the design requirements.

Manifold 25 and strain relief 26 are connected to the proximal end of metallic tube 11 by a suitable medical grade adhesive such as a urethane or an epoxy adhesive. Manifold 25 is preferably made of polycarbonate and is injection molded. Strain relief 26 is preferably made of a polyolefin such as a polyolefin copolymer or high density polyethylene and is preferably made by an extrusion process. Manifold 25 includes standard lure threads at the proximal end to facilitate fluid connection to an inflation device (not shown). Those skilled in the art will recognize that other suitable manifolds and strain reliefs may be employed to accomplish the same tasks.

Polymer guide wire tube 12 is preferably made of an extruded polymer such as high density polyethylene but may also be made of a thermoset polymer such as polyimide. Polymer guide wire tube 12 may include an exterior lubricious coating such as PTFE or a silicone based coating and may also include an internal coating to reduce the friction between the inside surface of the polymer guide wire tube 12 and the exterior surface of a guide wire (not shown). The polymer guide wire tube 12 is connected at its distal end to the distal balloon waste 17 of the balloon 16 by means of a suitable adhesive such as cyanoacrylate or epoxy. As best seen in FIG. 5, the polymer guide wire tube 12 is nested in the crimp of distal polymer tube 13 with the proximal balloon waste 18 surrounding both the polymer guide wire tube 12 and the distal polymer tube 13. A suitable adhesive 19 is used to create a mechanical and fluid seal around the polymer guide wire tube 12. The polymer guide wire tube 12 extends adjacent the distal polymer tube 13 and the metallic tube 11. The polymer guide wire tube 12 may be connected to either or both the metallic tube 11 and the distal polymer tube 13 by means of a suitable adhesive. Alternatively, polymer guide wire tube 12 may remain unconnected to either the metallic tube 11 or the distal polymer tube 13.

Core wire 14 is connected to the distal end of the metallic tube 11 by means of a suitable weld joint or solder joint. Preferably, a short longitudinal slot is made in the distal end of the metallic tube 11 to facilitate connection of guide wire 14. The slot is preferably a width slightly smaller than the diameter of the proximal end of the core wire 14. As such, core wire 14 may be connected inside the lumen of metallic tube 11 in an off-axis position, thus allowing for the passage of inflation fluid without substantially increasing the profile at the junction point. Core wire 14 is preferably made of 304 V stainless steel and includes a series of tapers along its length made by a suitable process such as centerless grinding. The distal end of the core wire 14 may be stamp-formed into a ribbon to facilitate insertion between the marker band 15 and the polymer guide wire tube 12 under the balloon. A suitable adhesive such as cyanoacrylate facilitates connection between the distal end of the core wire 14 and the marker band 15. Core wire 14 is preferably 0.012" diameter at the proximal end and may taper to approximately 0.005" diameter adjacent the proximal balloon waste 18. The overall length of core wire 14 is preferably about 9"–12". Those skilled in the art will recognize that other suitable dimensions, materials and manufacturing methods may be employed to accomplish the same result.

Distal polymer tube 13 is preferably made of a polyolefin such as high density polyethylene, but may also be made of other suitable materials such as a thermoset polymer (e.g., polyimide). The distal polymer tube is preferably made by an extrusion process and may incorporate tapers along its length formed by pulling the extruded tube through a heated die. The crimp in the distal end of the distal polymer tube 13 may be formed by inserting the distal end of the tube 13 into a slot and partially compressing the tube radially with a rounded blade. Those skilled in the art will recognize that other suitable materials, dimensions and manufacturing processes may be employed.

The inflatable balloon 16 is preferably made of a polyolefin such as a polyolefin copolymer and is formed by blow-molding an extruded and irradiated tube. Other suitable materials such as PET, nylon and HDPE may be employed to manufacture the balloon 16.

Radiopaque marker band 15 is preferably made of a metallic alloy such as 90% platinum, 10% iridium and is bonded to the distal end of the polymer guide wire tube 12 by a suitable adhesive such as cyanoacrylate. The radiopaque marker band preferably has a length of 0.051" and inside diameter of preferably about 0.022" and a wall thickness of preferably about 0.003". Those skilled in the art will recognize that other suitable materials, such as gold, and other suitable dimensions may be employed.

Figure 2:
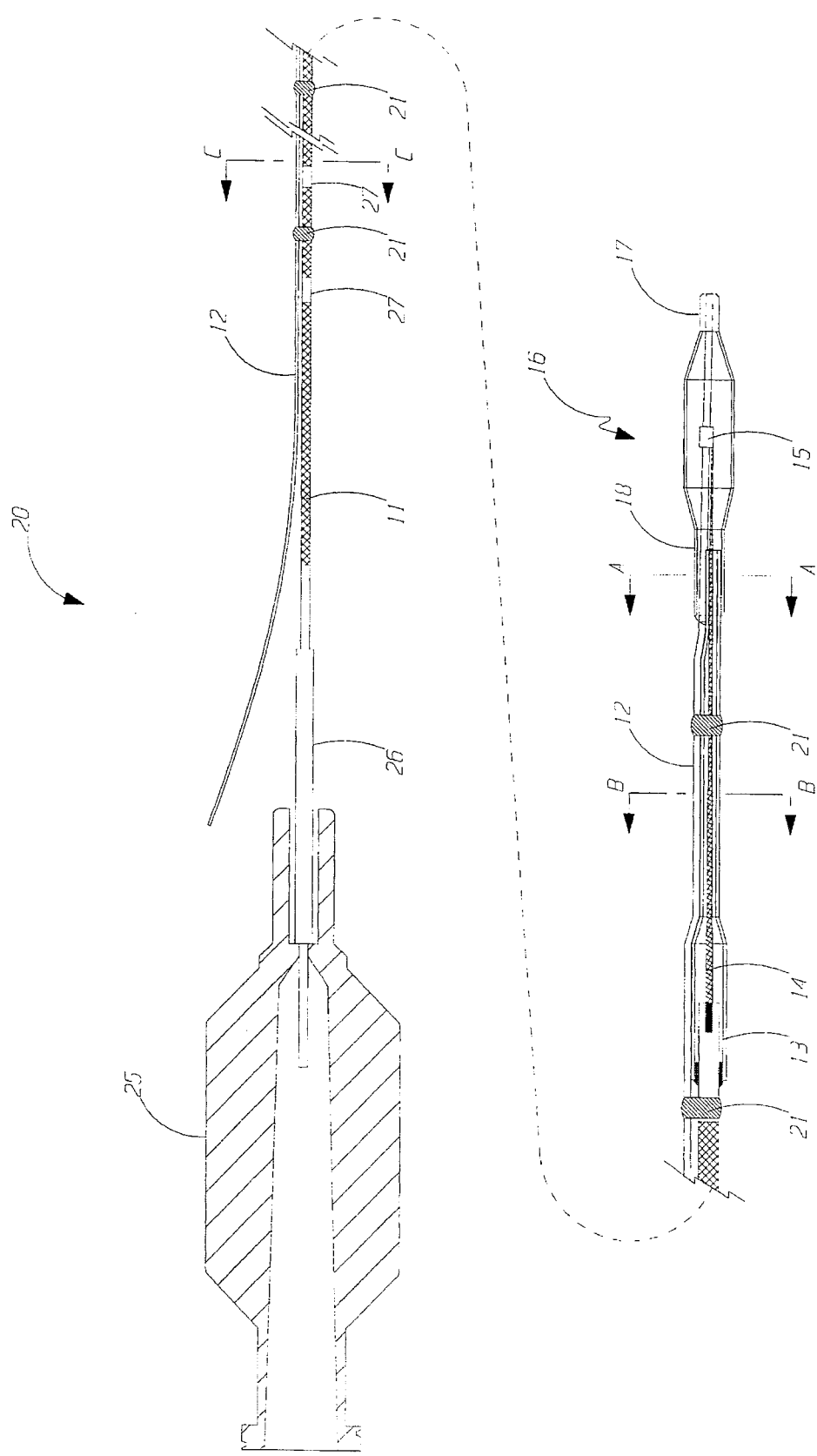
FIG. 2 is a partially longitudinally sectioned view of a second embodiment of the present invention.

Referring now to FIG. 2, a second embodiment of the present invention is shown. The above discussion with reference to FIG. 1 is equally applicable to FIG. 2 with the following exceptions. Catheter 20 may incorporate a series of connection rings 21. The connection rings 21 serve to connect the polymer guide wire tube 12 to the distal polymer tube 13 and the metallic tube 11. The connection rings 21 ultimately function to guide the catheter 20 substantially parallel to a guide wire (not shown) inserted into the polymer guide wire tube 12. This may serve to enhance the navigability and crossability of the catheter 20. Connection rings 21 may be made of any suitable thin walled polymer tube section such as polyethylene, polyolefin or polyimide, but a heat-shrinkable polymer is preferred. Connection rings 21 may be secured to the polymer guide wire tube 12, the distal polymer tube 13 and the metallic tube 11 by a suitable adhesive such as cyanoacrylate. Although adhesive is preferred to secure the connection rings 21 along the catheter shaft, adhesive may not be necessary if the one wishes to be able to move the connection rings 21 or if the connection rings 21 sufficiently secure due to friction. Preferably, the connection rings 21 do not substantially add to the overall profile of the catheter 20. The connection rings 21 are preferably on the order of 0.25 inches long but may range between 0.0625 and 0.50 inches long. The connection rings 21 are preferably spaced 1.0 inch apart but may be placed closer together or further apart as deemed necessary.

Figure 3:
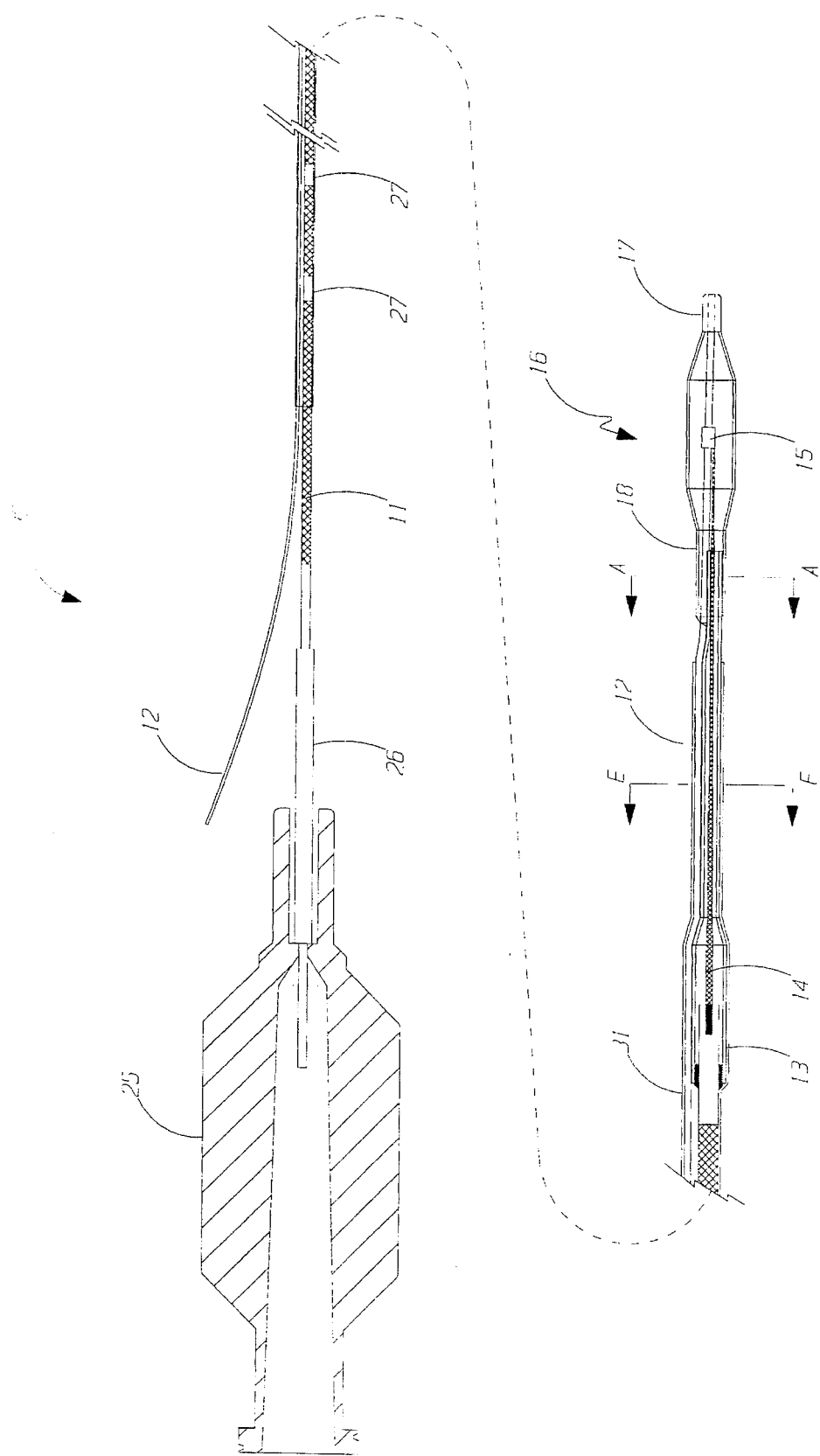
FIG. 3 is a partially longitudinally sectioned view of a third embodiment of the present invention.

Referring now to FIG. 3, a third embodiment of the present invention is shown. The above discussion with reference to FIG. 1 is equally applicable to FIG. 3 with the following exceptions. Catheter 30 may incorporate a connection sleeve 31 to secure the polymer guide wire tube 12 to the metallic tube 11 and the distal polymer tube 13. The connection sleeve 31 serves substantially the same function of connection rings 21 as discussed with reference to FIG. 2. Connection sleeve 31 is preferably made of a heat-shrinkable polymer such as irradiated polyolefin and is heat-shrunk around the catheter shaft to substantially conform to the outer profile of the catheter 30, as best seen in the cross-sectional drawing shown in FIG. 9 taken at section E—E in FIG. 3. As with the connection rings 21 referred to in FIG. 2, the connection sleeve 31 may be made of several different materials. In addition, the connection sleeve 31 may be a single elongate piece or a plurality of pieces spaced along the catheter shaft. A suitable adhesive such as a cyanoacrylate may be employed to secure the connection sleeve 31 to the catheter shaft. The distal end of the connection sleeve 31 is preferably sealed to the catheter shaft with adhesive to prevent bodily fluids such as blood from flowing under the sleeve 31.

Figure 4:
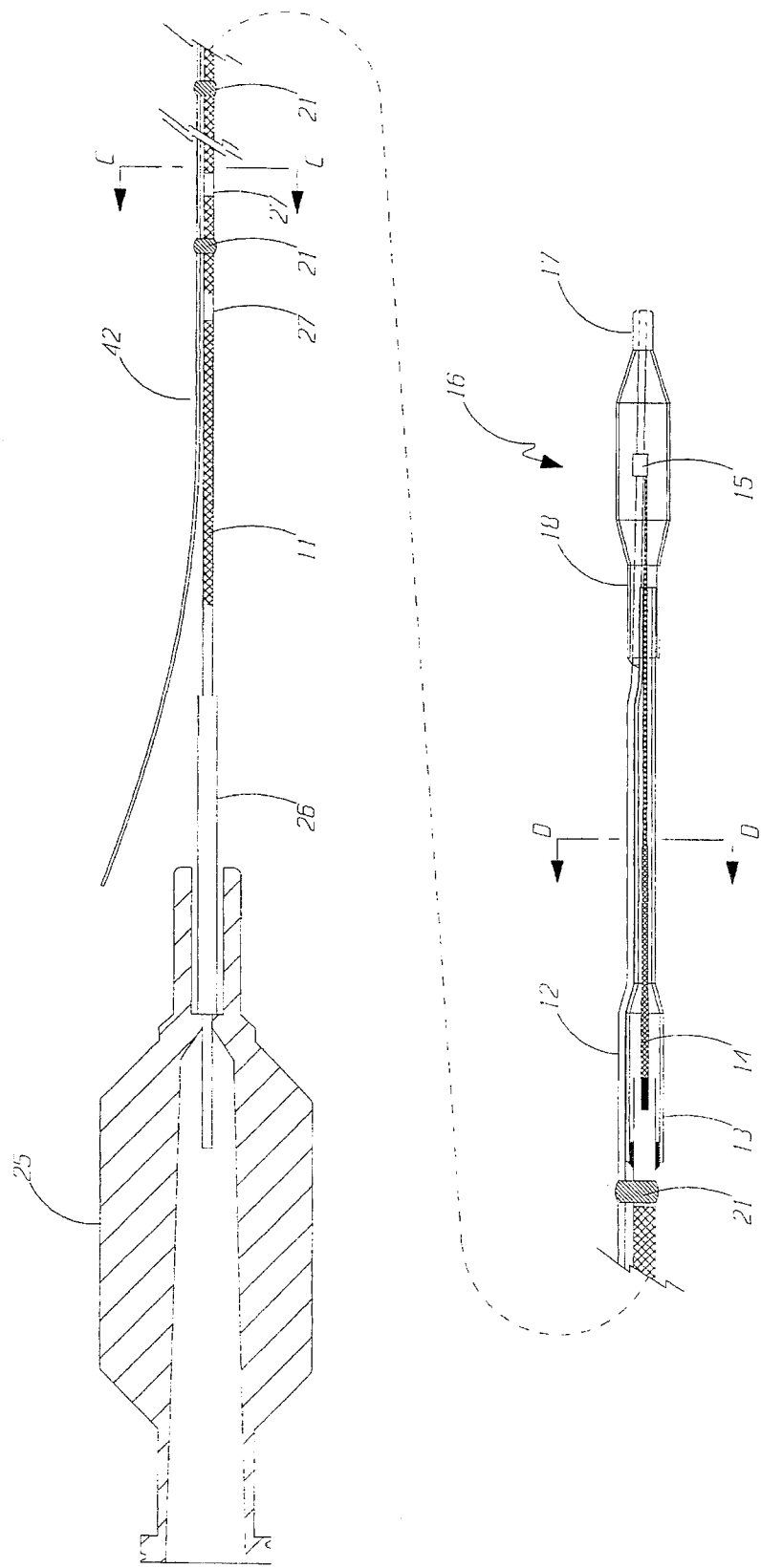
FIG. 4 is a partially longitudinally sectioned view of a fourth embodiment of the present invention.
Figure 8:
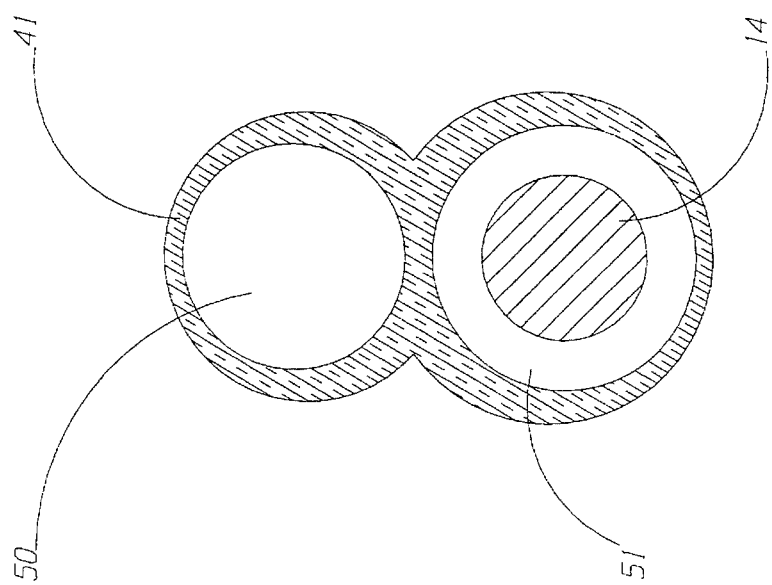
FIG. 8 is a latitudinally sectioned view taken at D—D in FIG. 4.

Referring now to FIG. 4, a fourth embodiment of the present invention is shown. The above discussion with reference to FIG. 1 is equally applicable to FIG. 4 with the following exceptions. Catheter 40 incorporates a dual lumen extruded tube to comprise a distal polymer extrusion 41 and a skived extrusion guide wire tube 42. The dual lumen extrusion of catheter 40 replaces the two separate tubes comprising the distal polymer tube 13 and polymer guide wire tube 12 as discussed with reference to FIG. 1. The dual lumen extrusion negates the need to provide connection rings or a connection sleeve on the distal end of the catheter 40. The distal polymer extrusion 41 includes a guide wire lumen 50 and an inflation lumen 51 with core wire 14 extending therethrough, as best shown in FIG. 8. The skived extrusion guide wire tube 42 is made by cutting away the portion of the dual lumen extrusion comprising the inflation lumen 51. The skived extrusion guide wire tube 42 may be connected to the metallic tube 11 by a suitable adhesive, by connection rings 21, or by connection sleeve 31 as discussed with reference to FIGS. 2 and 3, respectively. It should be noted however, that a connection between the skived extrusion guide wire tube 42 and the metallic tube 11 is not absolutely necessary but may be desirable depending on the functional characteristics desired.

In practice, the catheter 10, 20, 30 or 40 is preferably used in a manner similar to that of a conventional OTW catheter, while making the necessary handling adjustments due to the enhanced performance characteristics described previously.

While the specification describes the preferred constructions, methods and materials of manufacture and methods of practice, those skilled in the art will appreciate the scope and spirit of the invention with reference to the appended claims.

What is claimed is:

1. A balloon dilation catheter system, comprising:
   (i) a metallic tube having a proximal end, a distal end, and a proximal inflation lumen extending therethrough;
   (ii) a polymer guide wire tube having a proximal end, a distal end, an exterior surface, and a guide wire lumen extending therethrough, the polymer guide wire tube extending exteriorly and parallel with the metallic tube, the proximal end of the polymer guide wire tube extending proximally to a point near the proximal end of the metallic tube, the distal end of the polymer guide wire tube extending distally beyond the distal end of the metallic tube;
   (iii) a core wire having a proximal end and a distal end, the proximal end of the core wire rigidly secured to the distal end of the metallic tube;
   (iv) a distal polymer tube having a proximal end, a distal end, and a distal inflation lumen extending therethrough, the distal polymer tube extending exteriorly and parallel with the polymer guide wire tube, the proximal end of the distal polymer tube connected to the distal end of the proximal metallic tube, a portion of the distal polymer tube connected to a portion of the polymer guide wire tube, the distal inflation lumen fluidly communicating with the proximal inflation lumen;
   (v) a balloon having a proximal end, a distal end, and a balloon inflation lumen extending therethrough, the proximal end of the balloon sealably connected to both the distal end of the distal polymer tube and a distal portion of the polymer guide wire tube, the distal end of the balloon sealably connected to the distal end of the polymer guide wire tube, the balloon inflation lumen fluidly communicating with the distal inflation lumen; and
   (vi) a removable guide wire slidably disposed in and extending through the guide wire lumen of the polymer guide wire tube.

2. A balloon dilation catheter system as in claim 1, further comprising a proximal sleeve disposed about and connecting the polymer guide wire tube and the metallic tube.

3. A balloon dilation catheter system as in claim 1, wherein the polymer guide wire tube is a dual-lumen extrusion further including a connection lumen extending therethrough, the metallic tube extending into the connection lumen.

4. A balloon dilation catheter as in claim 1, wherein the distal polymer tube and the polymer guide wire tube are integrally formed as a dual-lumen extrusion.

5. A balloon dilation catheter as in claim 1, wherein the distal end of the core wire is connected to one of the polymer guide wire tube, the distal polymer tube, and the balloon.

6. A balloon dilation catheter system, comprising:
   (i) a metallic tube having a proximal end, a distal end, an exterior surface, and a proximal inflation lumen extending therethrough;
   (ii) a polymer guide wire tube having a proximal end, a distal end, an exterior surface, and a guide wire lumen extending therethrough, the polymer guide wire tube extending exteriorly and parallel with the metallic tube, the proximal end of the polymer guide wire tube extending proximally to a point near the proximal end of the metallic tube, the distal end of the polymer guide wire tube extending distally beyond the distal end of the metallic tube;
   (iii) a distal polymer tube having a proximal end, a distal end, an exterior surface, and a distal inflation lumen extending therethrough, the distal polymer tube extending exteriorly and parallel with the polymer guide wire tube, the proximal end of the distal polymer tube connected to the distal end of the proximal metallic tube, a portion of the exterior surface of the distal polymer tube connected to a portion of the exterior surface of the polymer guide wire tube, the distal inflation lumen fluidly communicating with the proximal inflation lumen;
   (iv) a balloon having a proximal end, a distal end, and a balloon inflation lumen extending therethrough, the proximal end of the balloon sealably connected to both the distal end of the distal polymer tube and a distal portion of the polymer guide wire tube, the distal end of the balloon sealably connected to the distal end of the polymer guide wire tube, the balloon inflation lumen fluidly communicating with the distal inflation lumen; and (v) a removable guide wire slidably disposed in and extending through the guide wire lumen of the polymer guide wire tube.

7. A balloon dilation catheter system as in claim 6, further comprising a proximal sleeve disposed about and connecting the polymer guide wire tube and the metallic tube.

8. A balloon dilation catheter system as in claim 6, wherein the polymer guide wire tube is a dual-lumen extrusion further including a connection lumen extending therethrough, the metallic tube extending through the connection lumen.

9. A balloon dilation catheter as in claim 6, wherein the distal polymer tube and the polymer guide wire tube are integrally formed as a dual-lumen extrusion.

10. A balloon dilation catheter system, comprising:

(i) a metallic tube having a proximal end, a distal end, an exterior surface, and a proximal inflation lumen extending therethrough;

(ii) a polymer guide wire tube having a proximal end, a distal end, an exterior surface, and a guide wire lumen extending therethrough, the polymer guide wire tube extending exteriorly and parallel with the metallic tube, the proximal end of the polymer guide wire tube extending proximally to a point near the proximal end of the metallic tube, the distal end of the polymer guide wire tube extending distally beyond the distal end of the metallic tube;

(iii) a distal polymer tube having a proximal end, a distal end, an exterior surface, and a distal inflation lumen extending therethrough, the distal polymer tube extending exteriorly and parallel with the polymer guide wire tube, the proximal end of the distal polymer tube connected to the distal end of the proximal metallic tube, a portion of the exterior surface of the distal polymer tube connected to a portion of the exterior surface of the polymer guide wire tube, the distal inflation lumen fluidly communicating with the proximal inflation lumen;

(iv) a balloon having a proximal end, a distal end, and a balloon inflation lumen extending therethrough, the proximal end of the balloon sealably connected to the distal end of the distal polymer tube, the distal end of the balloon sealably connected to the distal end of the polymer guide wire tube, the balloon inflation lumen fluidly communicating with the distal inflation lumen; and (v) a removable guide wire slidably disposed in and extending through the guide wire lumen of the polymer guide wire tube.

11. A balloon dilation catheter system as in claim 10, further comprising a proximal sleeve disposed about and connecting the polymer guide wire tube and the metallic tube.

12. A balloon dilation catheter system as in claim 10, wherein the polymer guide wire tube is a dual-lumen extrusion further including a connection lumen extending therethrough, the metallic tube extending through the connection lumen.

13. A balloon dilation catheter as in claim 10, wherein the distal polymer tube and the polymer guide wire tube are integrally formed as a dual-lumen extrusion.

14. A balloon dilation catheter as in claim 10, wherein the polymer guide wire tube and a proximal waist portion of the balloon extend coaxially.

15. A balloon dilation catheter as in claim 10, wherein a distal portion of the polymer guide wire tube and a distal portion of the distal polymer tube extend coaxially.

* * * * *